United States Patent
Jung et al.

(10) Patent No.: US 9,518,039 B2
(45) Date of Patent: Dec. 13, 2016

(54) POLYMER-FIXED DERIVATIVES OF DITHIOLANE OR DITHIANE

(71) Applicant: KARLSRUHER INSTITUT FUER TECHNOLOGIE, Karlsruhe (DE)

(72) Inventors: Nicole Jung, Mannheim (DE); Simone Graessle, Gaggenau (DE); Stefan Braese, Troisdorf (DE)

(73) Assignee: KARLSRUHER INSTITUT FUER TECHNOLOGIE, Karlsruhe (DE)

( * ) Notice: Subject to any disclaimer, the term of this patent is extended or adjusted under 35 U.S.C. 154(b) by 0 days.

(21) Appl. No.: 15/023,801

(22) PCT Filed: Sep. 23, 2014

(86) PCT No.: PCT/EP2014/070186
§ 371 (c)(1),
(2) Date: Mar. 22, 2016

(87) PCT Pub. No.: WO2015/044108
PCT Pub. Date: Apr. 2, 2015

(65) Prior Publication Data
US 2016/0229832 A1     Aug. 11, 2016

(30) Foreign Application Priority Data
Sep. 27, 2013   (DE) .................. 10 2013 110 740

(51) Int. Cl.
| C07D 339/00 | (2006.01) |
| C07D 339/06 | (2006.01) |
| C07D 339/08 | (2006.01) |
| C07D 235/18 | (2006.01) |
| C07D 409/04 | (2006.01) |
| C07F 5/02   | (2006.01) |

(52) U.S. Cl.
CPC .......... C07D 339/06 (2013.01); C07D 235/18 (2013.01); C07D 339/08 (2013.01); C07D 409/04 (2013.01); C07F 5/022 (2013.01)

(58) Field of Classification Search
CPC combination set(s) only.
See application file for complete search history.

(56) References Cited

U.S. PATENT DOCUMENTS

| 4,256,644 A * | 3/1981 | Wachter ........ C07C 41/48 549/334 |
| 4,469,774 A | 9/1984 | Lee |
| 4,818,765 A | 4/1989 | Weith et al. |
| 4,946,861 A | 8/1990 | Weith et al. |
| 6,458,908 B1 | 10/2002 | Imai et al. |
| 8,349,536 B2 | 1/2013 | Nozaki |
| 2011/0076620 A1 | 3/2011 | Nozaki |

FOREIGN PATENT DOCUMENTS

| DE | 102006017492 A1 | 10/2007 |
| EP | 0099329 A1 | 1/1984 |
| EP | 1057808 A2 | 12/2000 |

OTHER PUBLICATIONS

C. Chen et al.: "Synthesis and photophysical studies of silylene-spaced divinylarene copolymers. Molecular weight dependent fluorescence of alternating silylene-divinylbenzene copolymers", J. Amer. Chem. Soc., vol. 119, No. 46, 1997, pp. 11321-11322.
Y.-J. Cheng et al.: "Intrachain energy transfer in silylene-spaced alternating donor-acceptor divinylarene copolymers", Chemical Communications, Aug. 7, 2002.
Synthetic Communications, vol. 34, No. 24, pp. 4545-4556, 2004.
Synthetic Communications, vol. 37:6, pp. 993-1000, 2007.

* cited by examiner

*Primary Examiner* — Nyeemah A Grazier
(74) *Attorney, Agent, or Firm* — Abel Law Group, LLP

(57) ABSTRACT

Derivatives of 1,3-dithianes and 1,3-dithiolanes of the general formula 1a

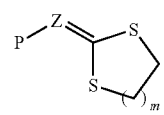

or salts thereof of the general formula 1b

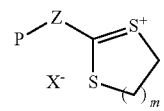

where P=polymeric support, m=1 or 2, Z is an organic linker or X=inorganic or organic anion, processes for preparation thereof and use thereof.

14 Claims, No Drawings

POLYMER-FIXED DERIVATIVES OF DITHIOLANE OR DITHIANE

All the documents cited in the present application are incorporated into the present disclosure by reference in their entirety.

BACKGROUND OF THE INVENTION

1. Field of the Invention

The present invention relates to solid phase-fixed dithiolanylium salts and dithianylium salts and ylidene-dithianes and ylidene-dithiolanes, to the preparation thereof and to the use thereof.

2. Discussion of Background Information

Dithianes or dithiolanes and their oxo derivatives are known from the prior art. For example, U.S. Pat. No. 4,946,861 describes dithianylidenes and the oxides thereof and the use thereof as pharmaceuticals.

It is known that dithianes or dithiolanes can be used for the conversion of ketones or aldehydes. This affects applications including the following:
1) as protecting groups in protecting group strategies
2) as a necessary transformation in the umpolung reaction
3) as an intermediate for further derivatization, for example introduction of fluorine.

The transformation of the carbonyl functionality to give the dithiolane and to give the dithiane is a reaction that can be conducted with good to very good yields, but which generally has the following disadvantages:
1) the reagents are toxic
2) the reagents stink to high heaven
3) the products have to be purified in a complex manner after the reaction
4) many reactions are not possible or run poorly, since the acid breaks down acid-labile groups in solution.

Synthetic Communications, Vol. 34, No. 24, pages 4545-4556, 2004 discloses use of 2-[1,3]dithian-2-ylidene-3-oxobutanamide as thioacetalization reagent in liquid phase reactions, wherein the workup of the products always also includes a chromatographic purification.

In the form of 2-(1,3-dithian-2-ylidene)malonic acid, Synthetic Communications, Vol. 37:6, pages 993-1000, 2007 discloses a similar substance for thioacetalization in liquid phase reactions.

What is common to the prior art is that the compounds disclosed are in unbound, i.e. unfixed, form and the reactions accordingly proceed entirely in liquid phase. Correspondingly, the disadvantages mentioned occur.

SUMMARY OF THE INVENTION

Problem

The problem addressed by the present invention is that of avoiding the disadvantages of the prior art, especially of providing reagents that are very easy to handle, which do not have the disadvantages of the prior art, and processes for preparation thereof and the use thereof.

The intention was likewise to find new chemicals which can be obtained with the aid of the compounds of the invention.

Another intention was to use the compounds of the invention to find new access routes to chemicals, especially novel chemicals.

Solution

This problem is solved by the compounds, the processes and the uses according to the description and the claims.

DEFINITIONS OF TERMS

In the context of the present invention, all stated amounts should be understood as statements of weight, unless stated otherwise.

In the context of the present invention, the term "room temperature" means a temperature of 20° C. Temperature figures, unless stated otherwise, are in degrees Celsius (° C.).

Unless stated otherwise, reactions or process steps cited are conducted at standard pressure/atmospheric pressure, i.e. at 1013 mbar.

In the context of the present invention, the wording "and/or" includes both any desired element and all combinations of the elements listed in the particular list.

DETAILED DESCRIPTION

The present invention provides derivatives of 1,3-dithianes or 1,3-dithiolanes of the general formula 1a

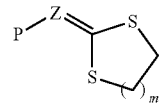

or salts thereof of the general formula 1b

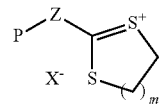

where
P=polymeric support,
m=1 or 2,
Z=organic linker of any length which binds the dithiolane/dithiane unit of 1a via a double bond or binds the dithiolane/dithiane unit of 1 b via a single bond to the polymeric support,
X=inorganic or organic anion.

These are also referred to generally in the context of the present invention as the inventive compounds or inventive reagents.

Preferably, Z is selected from the group consisting of the organic radicals
—$CH_2$—Y—$(CH_2)_n$—$CH_2$—, —$CH_2$—Y—$(CH_2)_n$—CH=,
—$CH_2$—Y—CO—$(CH_2)_n$—$CH_2$—, —$CH_2$—Y—CO—$(CH_2)_n$—CH=
—$CH_2$—NH—$C_6H_4$—Y—$(CH_2)_n$—$CH_2$— or —$CH_2$—NH—$C_6H_4$—Y—$(CH_2)_n$—CH=,
more preferably selected from the group consisting of the organic radicals
—$CH_2$—Y—$(CH_2)_n$—$CH_2$—, —$CH_2$—Y—$(CH_2)_n$—CH=,
—$CH_2$—Y—CO—$(CH_2)_n$—$CH_2$— or —$CH_2$—Y—CO—$(CH_2)_n$—CH= where
Y=NH or O,
n=0 to 10.

Preferably, n=1 or 2.

Preferably, X is selected from the group consisting of the anions Br$^-$, Cl$^-$, Br$_3^-$, ClO$_4^-$, HCl$_2^-$, BF$_4^-$, CF$_3$SO$_3^-$, especially BF$_4^-$, CF$_3$SO$_3^-$.

Preferably, P is selected from the group consisting of polystyrene, polypropylene, polyethylene, polyethylene terephthalate, silica and cellulose. Polystyrene is especially preferred.

In the context of the present invention, the polymeric support P is accordingly understood to mean the polymeric backbone or the polymeric structure without pendant functional groups.

It will be appreciated that it is also possible in the context of the present invention to use a plurality of different polymeric supports in a mixture.

It is likewise possible in the context of the present invention to use different Z groups (linker groups) in a mixture, optionally also together with mixtures of polymeric supports P.

Preferred inventive compounds are those selected from the group consisting of the compounds of the following formulae

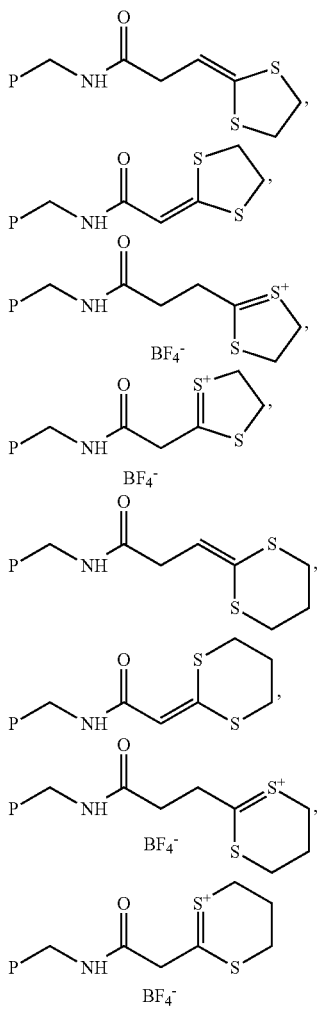

and mixtures thereof.

Particularly preferred compounds are those of the formula 1a in which
P=polystyrene, m=2, Z=—CH$_2$—Y—CO—(CH$_2$)$_n$—CH= with Y=NH,
and those salts of the formula 1b in which
P=polystyrene, m=2, Z=—CH$_2$—Y—CO—(CH$_2$)$_n$—CH$_2$— with Y=NH and X=BF$_4^-$,
where n is as defined above.

It will be appreciated that the present invention also encompasses variants in which the linker Z is bonded to the polymeric support P via double or triple bonds, rather than the single bond shown in the formulae. The present invention does of course further encompass products having a multitude of linker/dithiolane/dithiane units on a polymeric support; this is not shown in the formula representation for the sake of simplicity and better readability.

Correspondingly, it is also possible for different linkers Z to be bonded to a polymeric support via single, double and/or triple bonds.

The present invention also provides a process for preparing the inventive compounds.

The present invention provides a simple synthesis of the inventive compounds, wherein a solid support material is used, which then contains, through modification, both the thio unit and—if desired—acid.

The present invention therefore also provides a process for preparing the inventive compounds, comprising the process steps or consisting of the process steps of a) providing at least one polymeric support with pendant functional groups,
b) reacting the functional groups in the polymeric support(s) with at least one chain extender,
c) optionally modifying the functional groups of the chain-extended product resulting from b),
d) reacting the product obtained in b) or c) with optionally substituted aliphatic or aromatic dithio compounds having two or three carbon atoms between the sulfur atoms, preferably aliphatic dithio compounds, especially 1,2-dithioethane or 1,3-dithiopropane,
e) optionally working up the product obtained in step d)
   e1) to give the corresponding dithiolanylium salts/dithianylium salts (1b), preferably by washing using diethyl ether and THF,
   or
   e2) to give ylidene-dithiolanes/dithianes (1a), preferably by washing with other solvents than diethyl ether/THF or by adding base in the washing solvent.

The procedure for preparation of the inventive compounds is generally as follows:

First of all, at least one polymeric support, preferably one polymeric support, having pendant functional groups via which further radicals can be added on is provided.

If the polymeric support does not have the functional groups from the outset, the polymeric carrier can be functionalized by measures customary in the art.

The functional groups may, for example, be hydroxyl groups (especially in the case of silica as support) or amino groups (especially in the case of organic polymers such as polystyrene as support). Alternatively, they may equally be halogens or carbonyls in the broader sense (aldehydes/ketones/carboxylic acids or carbonyl chlorides) or the like.

Thereafter, chain extension is effected via reaction with the functional groups of the polymer with functional groups of another compound. In this case, however, it has to be ensured that a functional group remains at one end of the molecule. Examples of compounds of good suitability for this purpose are carboxylic anhydrides or dicarboxylic acids, which leave one carboxylic acid group. In addition, it is also possible to use dicarbonyl chlorides, diamines, diols or the like.

It is optionally possible to add a catalytically active compound.

The functional group which remains at the opposite end from the polymeric support can optionally be modified in order to be better suited to the subsequent reaction step. In the case of a carboxylic acid group, this may be, for example, modification with thionyl chloride to give the acid chloride group. In the subsequent reaction step (i.e. after chain extension and optional modification), reaction is effected with a dithio compound, preferably 1,2-dithioethane or 1,3-dithiopropane, which results, according to the reaction conditions, in the inventive polymeric support-bound 1,3-dithian-2-ylidenes and 1,3-dithiolan-2-ylidenes or the corresponding dithianylium and dithiolanylium salts.

In this step, it is also possible to use other dithio compounds if they have two or three carbon atoms between the two sulfur atoms. For example 1,2-dithiopropane, 1,3-dithiobutane or similar compounds.

In the context of the present invention, is it is advantageously also possible to proceed from already functionalized polymeric supports, since these are often commercially available. A preferred already functionalized polymeric support from which it is possible to proceed in the context of the present invention is polystyrene-$(CH_2NH_2)_x$ where x represents the number of pendant aminomethylene groups. It will be appreciated that other corresponding compounds are also usable, provided that they have corresponding functionalizations, for example polystyrene-$(CH_2Cl)_x$.

Especially preferred in accordance with the invention is a process comprising or consisting of the following process steps:
a) providing polystyrene with pendant —$CH_2$—$NH_2$ groups,
b) reacting with succinic anhydride in dimethylformamide (DMF) and/or triethylamine,
   optionally in the presence of 4-(dimethylamino)pyridine (DMAP),
c) reacting the resulting carboxylic acid with thionyl chloride to give the acid chloride,
d) reacting with 1,2-dithioethane or 1,3-dithiopropane in the presence of $HBF_4$ in diethyl ether,
e) optionally working up the product obtained in step d) by removing the solvent and washing the remaining resin, preferably with diethyl ether and/or THF, and then drying the resin.

In one variant, it is preferable to conduct the reaction in step b) in the presence of DMAP.

A further particularly preferred process of the invention comprises or consists of the following steps:
a) providing polystyrene with pendant —$CH_2$—$NH_2$ groups,
b) reacting with adipoyl dichloride in triethylamine, optionally in the presence of 4-(dimethylamino)pyridine (DMAP),
d) reacting with 1,2-dithioethane or 1,3-dithiopropane in the presence of $HBF_4$ in diethyl ether,
e) optionally working up the product obtained in step d) by removing the solvent and washing the remaining resin, preferably with diethyl ether and/or THF, and then drying the resin.

In one variant, it is preferable to conduct the reaction in step b) in the presence of DMAP.

The preferred reaction of a carboxylic anhydride with a pendant amine group on the polymeric support (for example in the form of an aminomethylene group) is particularly advantageous because it firstly enables the attachment of the sulfur moiety and, secondly, the linker or the attached derivative remains stable even in the course of the acidic chlorination reaction and the salt formation which is conducted under acidic conditions.

The workup of the product obtained in step d) can be optimized by choice of the solvents such that the salt in the solid phase is conserved. Salts on the polymeric support are rare and are also difficult to maintain through the wash steps.

More particularly, the procedure in the context of the present invention may be as follows: the reaction mixture is transferred into a frit, the solvent is removed via filtration and the remaining resin is washed with solvent until it is odor-neutral. Particular preference is given here to diethyl ether and THF (unlike other solvents, these solvents keep the salt on the resin intact). The resin is then dried under high vacuum.

Correspondingly, in a preferred variant of the present invention, the workup step e) is obligatory.

Finally, the present invention provides for the various uses of the inventive compounds or of the compounds prepared by the process of the invention.

The compounds of the invention can also be referred to or used as dithioalkyl reagents.

The inventive compounds are dithianylium and dithiolanylium salts and 1,3-dithian- or 1,3-dithiolan-2-ylidenes.

The linkers Z used in accordance with the invention serve for attachment of the thio components to the polymeric support. Preferably, for attachment to the polymeric support, they have structures which remain stable in the reaction in the preparation of the inventive compounds during the acidic chlorination reaction and the salt formation which is conducted under acidic conditions.

For this purpose, preference is given to using linkers Z bonded to the polymeric support via a C—C or a C—N linkage. Amide groups are of very good suitability for this purpose.

Particular preference is given in accordance with the invention to the above-specified linkers Z.

It will be appreciated that it is possible in the context of the present invention to obtain the linkers Z by reaction with various substances. For example also by reaction with amino acids (such as beta- or gamma-amino acids).

By means of the inventive compounds, it is possible to achieve excellent results in the field of organic chemistry, for example in catalysis and also for stoichiometric conversions; for instance, it is possible to introduce protecting groups particularly easily and conduct reactions with $HBF_4$ in a particularly simple and economically viable manner.

The inventive compounds have the following advantages:
1) the inventive compounds/reagents are nontoxic and easy to handle/dose by virtue of solid attachment to the support material;
2) the inventive compounds/reagents, because of the immobilization on the polymeric support, have virtually no odor emissions, but are (completely) odor-neutral;
3) a very high percentage of the reactions conducted with the inventive compounds/reagents need not include any complex purification step after the reaction. No chromatography is necessary; in most cases, simple removal of the polymer by filtration and concentration of the reaction mixture by rotary evaporation are sufficient.

The high purity of the products obtained by means of the inventive compounds/reagents is based on the exceptional properties of the present invention compared to the prior art:

According to the prior art, conversions in the liquid phase either usually do not run to absolute completion and still include some starting material after the reaction through the stoichiometric addition of the reagents, or still contain reagent which has to be removed in the event of addition in excess. The acid added catalytically is also still present in the crude mixture.

In the case of the inventive compounds/reagents, both the thio component (bound to polymeric support) and the acid (also bound to polymeric support) can be added in excess. This promotes full conversion. However, the excess, in contrast to the prior art, does not lead to contamination of the mixture since it is only when the carbonyl is attacked that the two components are detached from the polymeric support.

The acid released during the reaction (e.g. $HBF_4$) remains immobilized on the support material after the reaction has ended and in this way does not get into the product mixture.

4) With the inventive compounds, it is possible to conduct reactions where a basic environment is generated by addition of bases in the liquid phase (e.g. carbonates), while the inventive compounds 1b on the support are at least partly conserved. Thus, it is also possible to convert compounds containing acid-labile groups to the dithiolane/dithiane.

5) The inventive compounds/reagents are easy and inexpensive to produce.

6) Reactions conducted with the inventive compounds/reagents lead to very good yields which are higher in most cases than in the prior art reactions.

The particular advantages of the present invention are achieved because, in contrast to the prior art, the reactions with the inventive compounds/reagents are not pure liquid phase reactions; instead, the fixing of the thio component via a linker group on a polymeric support gives rise to a solid reagent phase.

Therefore, an essential aspect of the present invention is that the inventive compounds are used as solid phase reagents.

In the form of the inventive compounds, a middle way has surprisingly been found between very stable attachment to the resin (good because it is odor-free, easy to prepare and stable) and easy transfer of the thiol moiety (good and quick reaction outcomes).

It is a further advantage of the inventive compounds that, when they are used to introduce thioacetal protecting groups into aldehydes/ketones, the reaction is not water-sensitive, and (small) amounts of water are instead tolerated; the apparatuses thus need not be dried beforehand. In addition, the reactions can be conducted in standard atmosphere; the presence of inert gas is unnecessary.

The inventive compounds can be used in order to convert both aldehydes and ketones in such a way that a thioacetal or ketal group is introduced as protecting group.

In the case of the conversion of aldehydes, no further additives are needed.

In the case of the conversion of ketones, it is advantageous and therefore preferable under some circumstances to add an acid. Preference is given here to using Lewis acids which are also used for the liquid phase conversion of ketones to dithianes, for example $ZnCl_2$, $NiCl_2$, $CuCl_2$, etc.

A preferred example of a usable acid is $BF_3$, which is normally used in diethyl ether.

In the context of the present invention, it is possible for the first time to immobilize Lewis acids in combination with thio components.

The reactions to form dithianes/dithiolanes generally proceed within a period of time between 1 hour and 3 days, the exact reaction time of course being dependent on the respective reactants and the reaction conditions such as temperature and pressure. According to the invention, it is possible to accelerate the reactions by the action of microwave radiation, such that the reactions can then be concluded within less than 4 hours.

If ketones and aldehydes are present simultaneously and no additional acid is added, the reaction for protecting group introduction is chemoselective for the aldehydes by virtue of the inventive compounds.

Preferably in accordance with the invention, the conversion of the aldehydes and/or ketones proceeds in organic solvent. These are preferably selected from the group consisting of acetonitrile (MeCN), dichloromethane, trichloromethane, dimethylformamide (DMF), toluene, tetrahydrofuran (THF), methanol, ethanol and mixtures thereof. MeCN is especially preferred; the cleanest results are achieved therewith, which means a considerable advantage in terms of costs and in the workup.

It is preferable to use the inventive compounds, when they are used for introduction of protecting groups for aldehydes/ketones, in the form of the salts of formula 1b.

In general, the conversion of the aldehydes or ketones (the introduction of a protecting group into aldehydes or ketones) can be described as follows in the context of the present invention:

Aldehyde or ketone is dissolved in solvent and an inventive compound is added. In the case of conversion of ketones, an acid, preferably $BF_3$ in diethyl ether, is additionally added. The mixture is heated, preferably to reflux, and stirred or agitated (in a flask or closed glass vial) for a period of time, for example for 5 hours, until conversion of the starting material is complete, detected, for example, by thin layer chromatography.

The product can then be worked up as usual. According to the invention, preference is given to the following three variants:
a) The crude reaction product is applied to a frit, and the polymeric support is filtered off. The filtrates are then collected, for example, and the solvent is removed, for example by means of a rotary evaporator.
b) The crude reaction product is introduced into a separating funnel containing a mixture of organic solvent and water, preferably ethyl acetate and water (1:1). The different layers are separated and the organic phase is washed with water (for example 3 times). The organic phase is dried, for example with sodium sulfate, and the solvent is removed, for example by means of a rotary evaporator.
c) The crude reaction product is introduced into a separating funnel containing a mixture of organic solvent and water, preferably ethyl acetate and water (1:1). The different phases are separated and the organic phase is washed with water (for example 3 times). The organic phase is dried, for example with sodium sulfate, and the solids are removed by means of filtration. Thereafter, silica gel is added. The crude product is then purified by means of chromatography (e.g. column chromatography with hexane/ethyl acetate in various ratios as eluent).

By means of these reactions, the following novel substances were synthesized:
2-(1,3-dithian-2-yl)benzene-1,3-diol,
3',4'-dihydro-1'H-spiro[[1,3]dithiane-2,2'-naphthalene],
1-amino-2-(1,3-dithian-2-yl)anthracene-9,10(4aH,9aH)-dione,
(E)-ethyl 3-(1,3-dithiolan-2-yl)acrylate,
(E)-ethyl 3-(1,3-dithian-2-yl)acrylate;
these therefore also form part of the subject matter of the present invention.

The inventive compounds, especially when used as reagents, because of the fixing of the dithiane or dithiolane moieties on a polymer, are usable more flexibly than the prior art compounds, and the options in a wide variety of different reactions are extremely varied, for example for in situ fluorination as dithianes.

The inventive compounds containing bound acid can also be used for catalysis purposes. This is also true of those reactions which proceed independently of the thio component of the inventive component.

Further uses of the inventive compounds are (illustrative descriptions, the reaction in each case proceeding in solvent, preferably acetonitrile, and other inventive compounds also being usable):

1) Preparation of boranils, which are not known as such. The use thereof as fluorescent labels is of significance. The following three examples:

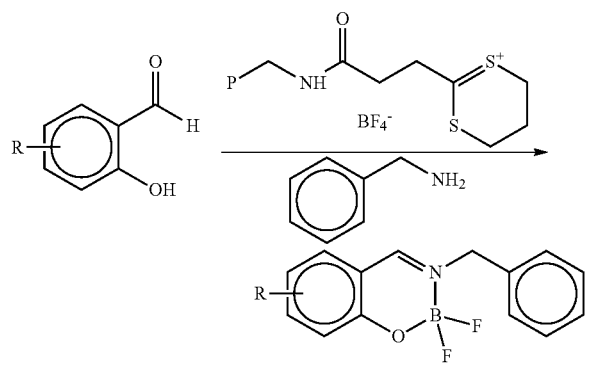

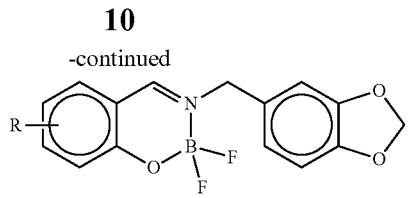

2) Conversion of 1,3-diketo compounds to stable BF$_2$ adducts which have very strong fluorescence.

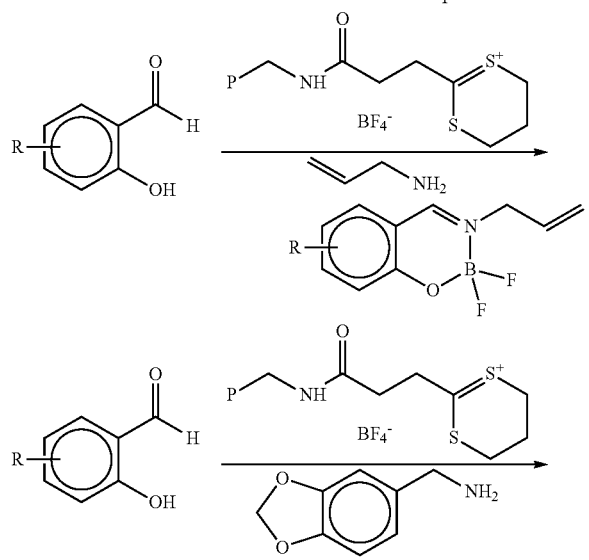

3) Preparation of benzimidazoles with addition of diaminobenzenes:

4) Deprotection of alcohols or amines protected with BOC, THP, silyl protecting groups.

A further possible use of the inventive compounds is the use thereof as ion exchangers, particularly using the compounds of the formula 1 b.

The various configurations of the present invention, but, for example, not exclusively those of the various dependent claims, can be combined with one another in any desired manner.

The invention is now elucidated with reference to the following nonlimiting examples:

EXAMPLES

Example 1

Preparation of the Compounds of General Formula 1a or Salts Thereof of General Formula 1b First Synthesis Variant Aminomethylpolystyrene resin (1.00 g; 1.34 mmol) was allowed to swell in chloroform (10 ml), and succinic anhydride (4.02 mmol; 3.00 equiv.), triethylamine (4.02 mmol; 3.00 equiv.) and DMAP (0.67 mmol; 0.50 equiv.) were added. The resin was agitated at 80° C. overnight. This turned the resin dark brown. For workup, the resin was washed with acetone (20 ml), water (20 ml), acetone (20 ml), methanol (20 ml), acetone (20 ml) and dichloromethane (2×20 ml), and dried first in a drying cabinet, then under high vacuum.

The product (1.00 g; 1.18 mmol) was then admixed with thionyl chloride (10 ml). The resin was agitated at 40° C. overnight. For workup, the resin was washed with dry diethyl ether (3×30 ml) and dried under high vacuum.

The resulting resin (1.02 g; 1.18 mmol) was allowed to swell under an argon atmosphere in abs. diethyl ether (10 ml), and propanedithiol (1.5 ml) and $HBF_4$ in diethyl ether (1.5 ml) were added. The reaction was agitated at 50° C. overnight. This turned the resin green. For workup, the resin was washed with diethyl ether (20 ml), THF (2×20 ml) and ether again (20 ml), and dried under high vacuum.

The synthesis route of the first variant can be represented in terms of formulae by way of example as follows (o=0 or 1):

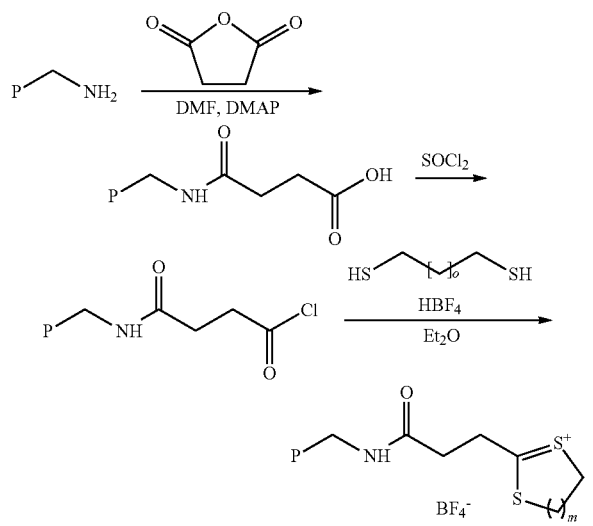

Second Synthesis Variant

Aminomethylpolystyrene resin (1.00 g; 1.34 mmol) was allowed to swell in chloroform (10 ml), and adipoyl dichloride (6.70 mmol; 5.00 equiv.), triethylamine (3.620 mmol; 2.70 equiv.) and DMAP (0.67 mmol; 0.50 equiv.) were added. The resin was agitated at 50° C. overnight. This turned the resin brown. For workup, the resin was washed with dry diethyl ether (100 ml) and dried under high vacuum.

The product (1.196 g; 1.334 mmol) was allowed to swell under an argon atmosphere in abs. diethyl ether (10 ml), and propanedithiol (1.5 ml) and $HBF_4$ in diethyl ether (1.5 ml) were added. The reaction was agitated at 50° C. overnight. This turned the resin green. For workup, the resin was washed with diethyl ether (20 ml), THF (2×20 ml) and dry diethyl ether again (20 ml), and dried under high vacuum.

Example 2

Method for Conversion of Aldehydes

To 0.1 mmol of the respective aldehyde compounds 1, 3 and 5 were added 200 mg of polymeric support material (compound A), and both were suspended in 2 ml of MeCN. The reaction was either heated to 80° C. or heated in a microwave (100° C., 1-3 bar, 50-200 watts).

After the reaction had ended, the polymer was separated from the reaction mixture via filtration and washing with acetone, the filtrate was concentrated on a rotary evaporator and the residue was dried. The substance was checked for purity by means of $^1H$ and $^{13}C$ NMR. The yields for compounds 1 and 3 were 95-100%, and for compound 5 80-85%.

The following compounds, divided into groups, were converted correspondingly; they were characterized by mass spectrometry or NMR spectroscopy and purification by chromatography:

Group 1: Aromatic Aldehydes

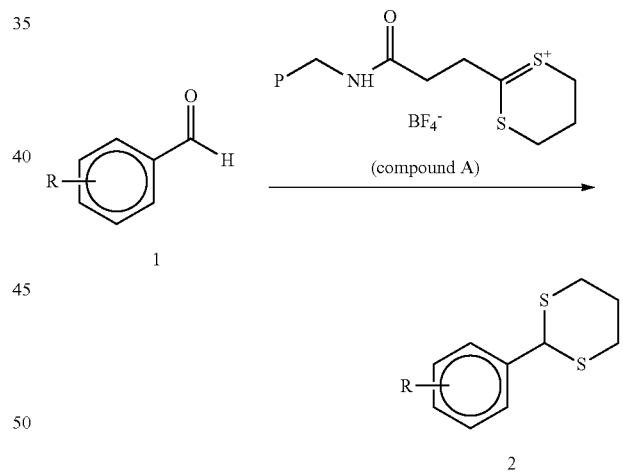

with R=OMe, OH, Ph, Oallyl, CN, $C_6H_5CH_2O$, H

Group 2: Aliphatic Aldehydes

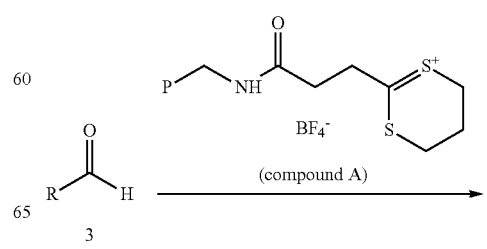

-continued

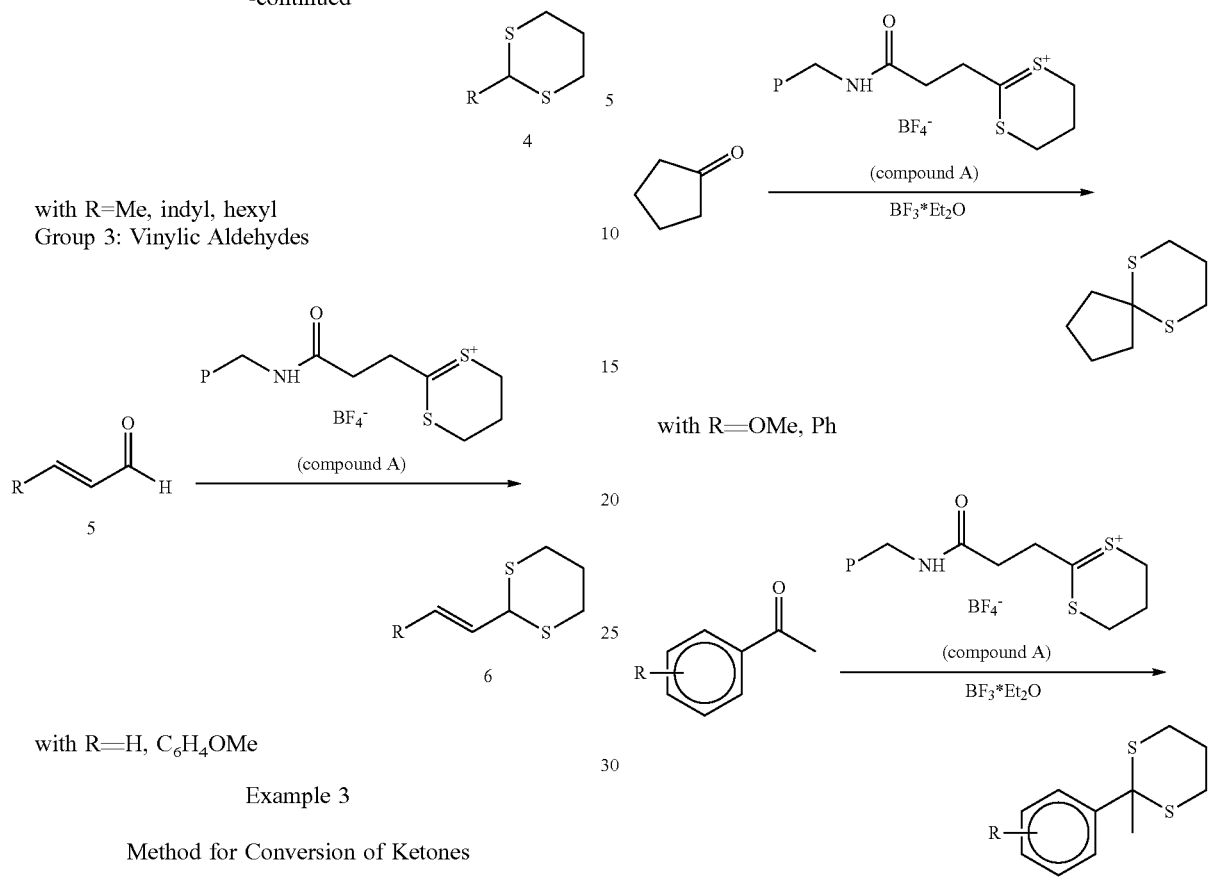

with R=Me, indyl, hexyl
Group 3: Vinylic Aldehydes with R=H, C$_6$H$_4$OMe with R=OMe, Ph The yield was 60%.

Example 3

Method for Conversion of Ketones

To 0.1 mmol of the particular ketone compound were added 200 mg of polymeric support material, and both were suspended in 2 ml of MeCN. 1 drop of BF$_3$*Et$_2$O was added. The reaction was either heated to 80° C. or heated in a microwave (100° C., 1-3 bar, 50-200 watts).

After the reaction had ended, the polymer was separated from the reaction mixture via filtration and washing with acetone, the filtrate was concentrated on a rotary evaporator and the residue was dried. The substance was checked for purity by means of $^1$H and $^{13}$C NMR.

The following compounds were converted correspondingly; they were characterized by mass spectrometry or NMR spectroscopy and purification (if required) by chromatography:

Example 4

Chemoselectivity

To check the chemoselectivity, the following reaction was conducted according to the above method for conversion of aldehydes (Example 2):

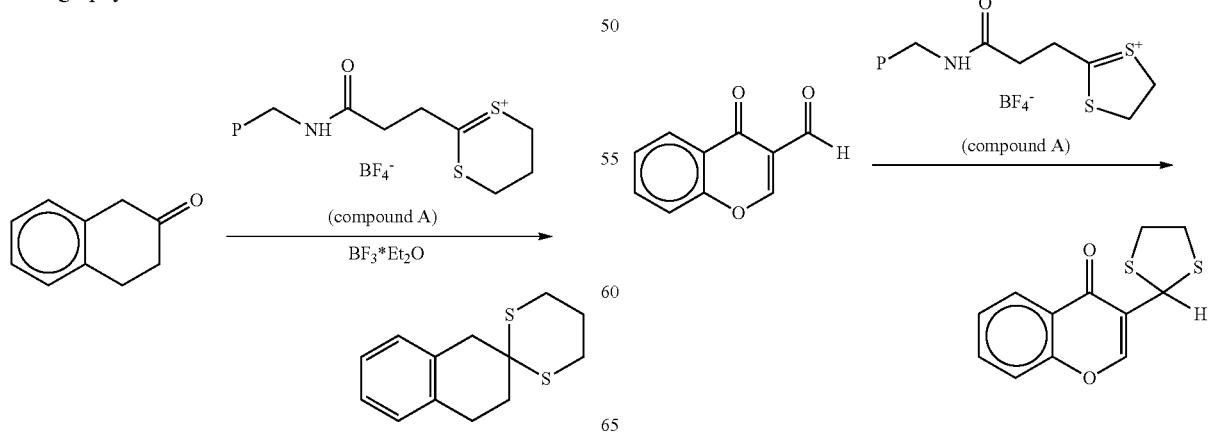

The yields were 95-100%.

There was exclusive conversion of the aldehyde group; the keto group was not converted.

By means of the present invention, the following protected aldehydes and ketones were prepared:
2-phenyl-1,3-dithiane
2-(1,3-dithian-2-yl)phenol
4-(1,3-dithian-2-yl)benzonitrile
2-(1,3-dithian-2-yl)benzene-1,3-diol
2-(4-(benzyloxy)phenyl)-1,3-dithiane
2-(4-(benzyloxy)phenyl)-1,3-dithiolane
4-(1,3-dithian-2-yl)-2-methoxyphenol
4-(1,3-dithiolan-2-yl)-2-methoxyphenol
2-([1,1'-biphenyl]-4-yl)-1,3-dithiane
2-(3-methoxyphenyl)-1,3-dithiane
2-(3-methoxyphenyl)-1,3-dithiolane
2-benzyl-1,3-dithiane
(E)-ethyl 3-(1,3-dithian-2-yl)acrylate
(E)-ethyl 3-(1,3-dithiolan-2-yl)acrylate
(E)-2-styryl-1,3-dithiane
(E)-2-(4-methoxystyryl)-1,3-dithiane
3-(1,3-dithiolan-2-yl)-4H-chromen-4-one
3-(1,3-dithian-2-yl)-4H-chromen-4-one
3',4'-dihydro-1H-spiro[[1,3]dithiane-2,2'-naphthalene]
1-amino-2-(1,3-dithian-2-yl)anthracene-9,10(4aH,9aH)-dione
9-(tert-butyl)-1,5-dithiaspiro[5.5]undecane.

What is claimed is:

1. A derivative of a 1,3-dithiane or 1,3-dithiolane of general formula 1a

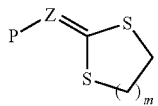

or a salt thereof of general formula 1b

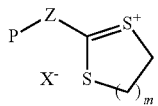

wherein
P=polymeric support,
m=1 or 2,
Z=organic linker of any length which binds the dithiolane/dithiane unit of general formula of 1a via a double bond or binds the dithiolane/dithiane unit of general formula of 1b via a single bond to the polymeric support P,
X=inorganic or organic anion.

2. The derivative of claim 1, wherein Z is selected from:
—$CH_2$—Y—$(CH_2)_n$—$CH_2$—, —$CH_2$—Y—$(CH_2)_n$—CH=,
—$CH_2$—Y—CO—$(CH_2)_n$—$CH_2$—, —$CH_2$—Y—CO—$(CH_2)_n$—CH=,
—$CH_2$—NH—$C_6H_4$—Y—$(CH_2)_n$—$CH_2$— or —$CH_2$—NH—$C_6H_4$—Y—$(CH_2)_n$—CH=,
where
Y=NH or O, and
n=0 to 10.

3. The derivative of claim 1, wherein Z is selected from:
—$CH_2$—Y—$(CH_2)_n$—$CH_2$—, —$CH_2$—Y—$(CH_2)_n$—CH=,
—$CH_2$—Y—CO—$(CH_2)_n$—$CH_2$—, or —$CH_2$—Y—CO—$(CH_2)_n$—CH=,
where
Y=NH or O, and
n=0 to 10.

4. The derivative of claim 2, wherein n=1 or 2.
5. The derivative of claim 3, wherein n=1 or 2.
6. The derivative of claim 1, wherein X is selected from $Br^-$, $Cl^-$, $Br_3^-$, $ClO_4^-$, $HCl_2^-$, $BF_4^-$, or $CF_3SO_3^-$.
7. The derivative of claim 1, wherein X is selected from $BF_4^-$ and $CF_3SO_3^-$.
8. The derivative of claim 1, wherein P is selected from one or more of polystyrene, polypropylene, polyethylene, polyethylene terephthalate, silica, or cellulose.
9. The derivative of claim 1, wherein P represents polystyrene.
10. The derivative of claim 5, wherein P represents polystyrene and X is selected from $BF_4^-$ and $CF_3SO_3^-$.
11. The derivative of claim 1, namely one or more of the following:

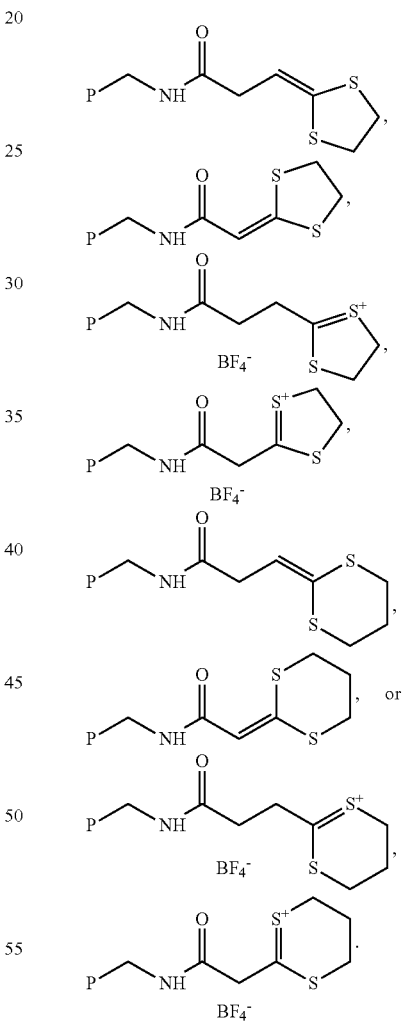

12. A process for preparing a derivative of claim 1, wherein the process comprises or consists of
(a) providing a polymeric support with pendant functional groups,
(b) reacting the functional groups in the polymeric support with a chain extender,
(c) optionally, modifying the functional groups of the chain-extended product resulting from (b), (d) reacting the product resulting from (b) or (c) with optionally substituted aliphatic or aromatic dithio compounds having one or two carbon atoms between the sulfur atoms, and
(e) optionally, working up the product resulting from (d)
  (e1) to afford a corresponding dithiolanylium salt/dithianylium salt (1b),
  or
  (e2) to afford a ylidene-dithiolane/dithiane (1a).

13. A process for preparing a derivative of claim 1 of formula (1b), wherein the process comprises or consists of
  (a) providing polystyrene with pendant —$CH_2$—$NH_2$ groups,
  (b) reacting the product of (a) with succinic anhydride in dimethylformamide and/or triethylamine and in the presence of 4-(dimethylamino)pyridine to result in a carboxylic acid,
  (c) reacting the carboxylic acid of (b) with thionyl chloride to afford the acid chloride,
  (d) reacting the acid chloride of (c) with 1,2-dithioethane or 1,3-dithiopropane in the presence of $HBF_4$ in diethyl ether, and
  (e) optionally, working up the product of (d) by removing the solvent and washing the remaining resin, followed by drying the resin.

14. A process for preparing a derivative of claim 1 of formula (1b), wherein the process comprises or consists of
  (a) providing polystyrene with pendant —$CH_2$—$NH_2$ groups,
  (b) reacting the product of (a) with adipoyl dichloride in dimethylformamide and/or triethylamine and in the presence of 4-(dimethylamino)pyridine (DMAP),
  (d) reacting the product of (b) with 1,2-dithioethane or 1,3-dithiopropane in the presence of $HBF_4$ in diethyl ether, and
  (e) optionally working up the product of (d) by removing the solvent and washing the remaining resin, followed by drying the resin.

* * * * *